United States Patent [19]
Kanda et al.

[11] Patent Number: 6,007,812
[45] Date of Patent: Dec. 28, 1999

[54] COMPOUND MK7634, PROCESS FOR PRODUCTION THEREOF, AND ANTHELMINTIC CONTAINING SAID SUBSTANCE

[75] Inventors: Mina Kanda; Noriko Chiba, both of Yokahoma; Shigenori Kumazawa, Ibaragi; Masayuki Takagi, Yokohama; Kenzo Harimaya, Yokohama; Tadaaki Okada, Yokohama, all of Japan

[73] Assignee: Mitsubishi Chemical Corporation, Tokyo, Japan

[21] Appl. No.: 08/849,301

[22] PCT Filed: Nov. 22, 1995

[86] PCT No.: PCT/JP95/02387

§ 371 Date: May 21, 1997

§ 102(e) Date: May 21, 1997

[87] PCT Pub. No.: WO96/16070

PCT Pub. Date: May 30, 1996

[30] Foreign Application Priority Data

Nov. 24, 1994 [JP] Japan .................................. 6-290057

[51] Int. Cl.⁶ .................................................. A61K 35/00
[52] U.S. Cl. ............................ 424/115; 435/41; 435/117; 435/118; 435/119
[58] Field of Search ............................. 424/115; 435/41, 435/117, 118, 119

[56] References Cited

FOREIGN PATENT DOCUMENTS

| WO 92/05191 | 4/1992 | European Pat. Off. . |
| 0 488 224 A2 | 6/1992 | European Pat. Off. . |
| 1434920 | 6/1966 | France . |

OTHER PUBLICATIONS

Moore–Landecker, E., "Fundamentals of the Fungi", 1982, Prentice Hall, pp. 257–268.
The Merck Index, 1996, pp. 1509–1510.
Betina, V. "Bioactive Secondary Metabolites of Microorganisms", 1995, Elsevier, pp. 172–173.
Laskin et al., "Handbook of Microbiology", vol. 5, CRC Press, 1977, p. 724.
The Merck Index, 1966, # 8991.

*Primary Examiner*—Irene Marx
*Attorney, Agent, or Firm*—Jones & Askew, LLP

[57] ABSTRACT

An imperfect fungus such as a microorganism belonging to the genus Curvularia in a culture medium containing nutrients utilizable for normal microorganisms and isolating MK7634 substance of a molecular formula: $C_8H_{15}N_3O_4$ from the culture by, for example, solvent extraction, ion exchange resin technique or gel filtration chromatography. The MK7634 substance can be used as an active ingredient of drugs. In particular, the MK7634 substance is a novel anthelmintic substance and expected to be used as an active ingredient of anthelmintics.

7 Claims, 4 Drawing Sheets ered to as MK7634 substance hereinafter), a process for
COMPOUND MK7634, PROCESS FOR PRODUCTION THEREOF, AND ANTHELMINTIC CONTAINING SAID SUBSTANCE

TECHNICAL FIELD

The present invention relates to MK7634 substance having anthelmintic activity, process for production thereof and use thereof as an anthelmintic containing it.

RELATED ART

Illnesses called parasitic diseases generally caused by parasites living on hosts and give serious damages to human and animal health and agriculture.

In order to treat or prevent such parasitic diseases, various drugs have hitherto been searched for. For example, as anthelmintically active substances derived from microorganisms, destomycin, hygromycin, avermectin and the like have been reported. However, number of such substances is very small. Accordingly, appearance of novel anthelmintically active substance is always demanded.

The present inventors provide a novel compound having anthelmintic activity, establish advantageous process for producing it and provide an anthelmintic containing the compound, thereby satisfying the above demand.

DESCRIPTION OF THE INVENTION

To satisfy the above demand, the present inventors continued a search of a substance having anthelmintic activity and found that a substance having anthelmintic activity is produced in a culture of a strain belonging to imperfect fungi. The present inventors isolated the active ingredient and determined physicochemical properties thereof and thus completed the present invention.

Therefore, the present invention relates to a substance exhibiting the following physicochemical properties (referred to as MK7634 substance hereinafter), a process for producing it and a drug, in particular an anthelmintic, containing the MK7634 substance as an active ingredient.

(1) Color and form: colorless powder
(2) Molecular formula: $C_8H_{15}N_3O_4$
(3) Specific rotation: $[\alpha]D^{25}=+32.8°$ (c=0.5, H2O)
(4) Mass spectrum (SI-MS): m/z 240 (MNa)+, 218 (MH)+
(5) Ultra-violet absorption spectrum: $\lambda$max ($H_2O$) nm=193(end absorption)
(6) Infra-red absorption spectrum: $\nu$max (KBr)cm$^{-1}$= 3400, 1670, 1630, 1405, 1350, 1090, 970
(7) Melting point: gradually colored and decomposed from 175° C.
(8) Solubility: soluble in water and insoluble in ether, chloroform and ethylacetate
(9) basicity, acidity and neutrality: basic
(10) Color reaction: positive in ninhydrin, GL and molybdic acid reactions
(11) Thin layer chromatography: Rf value is 0.3 (developing solvent is a mixed solvent of n-butanol, ethanol, chloroform and 17% ammonia (weight mixing ratio=4:5:2:5).

BEST MODE FOR CARRYING OUT THE INVENTION

Figure 1:
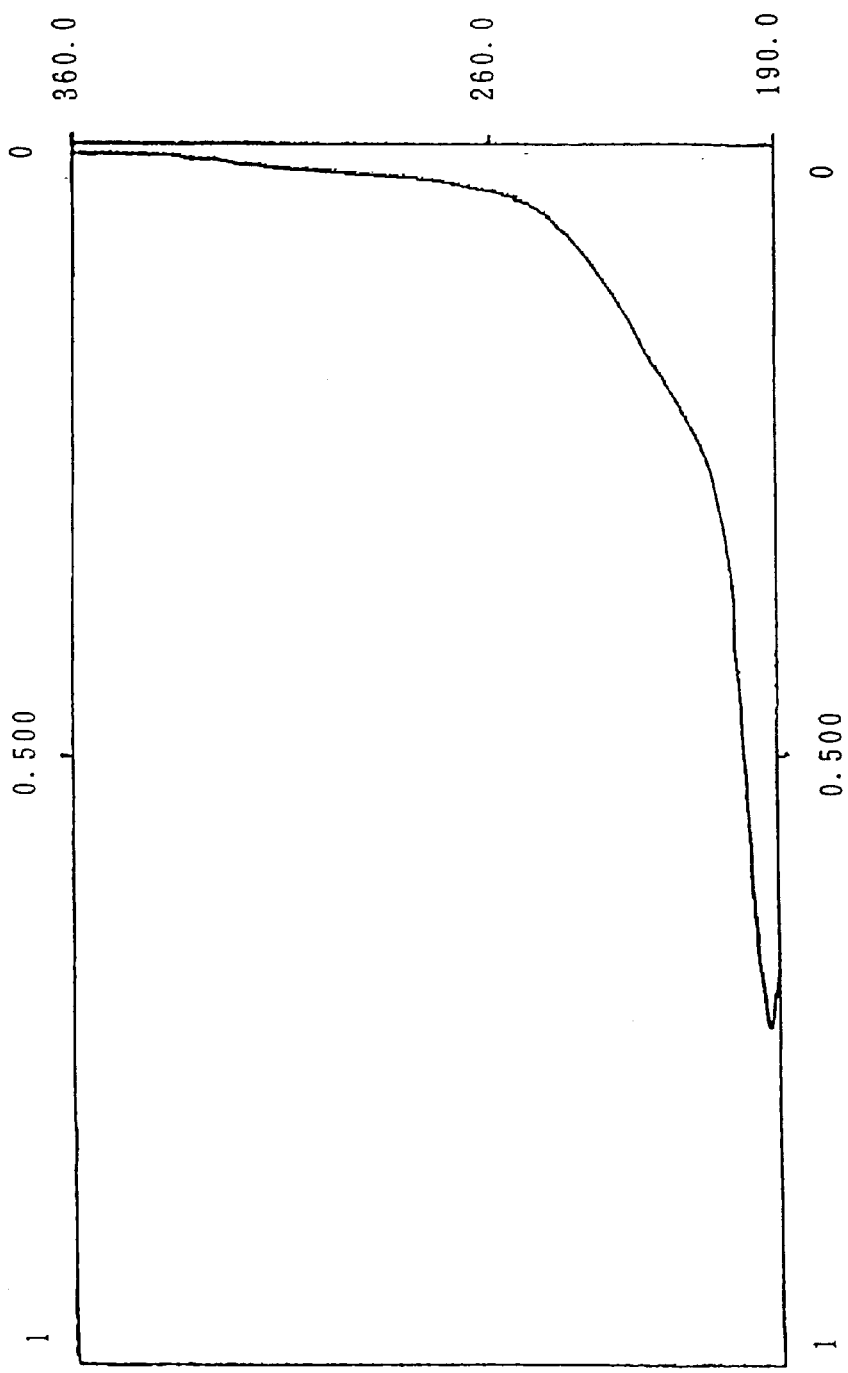
FIG. 1 shows UV spectrum of the MK7634 substance in an aqueous solution.
Figure 2:
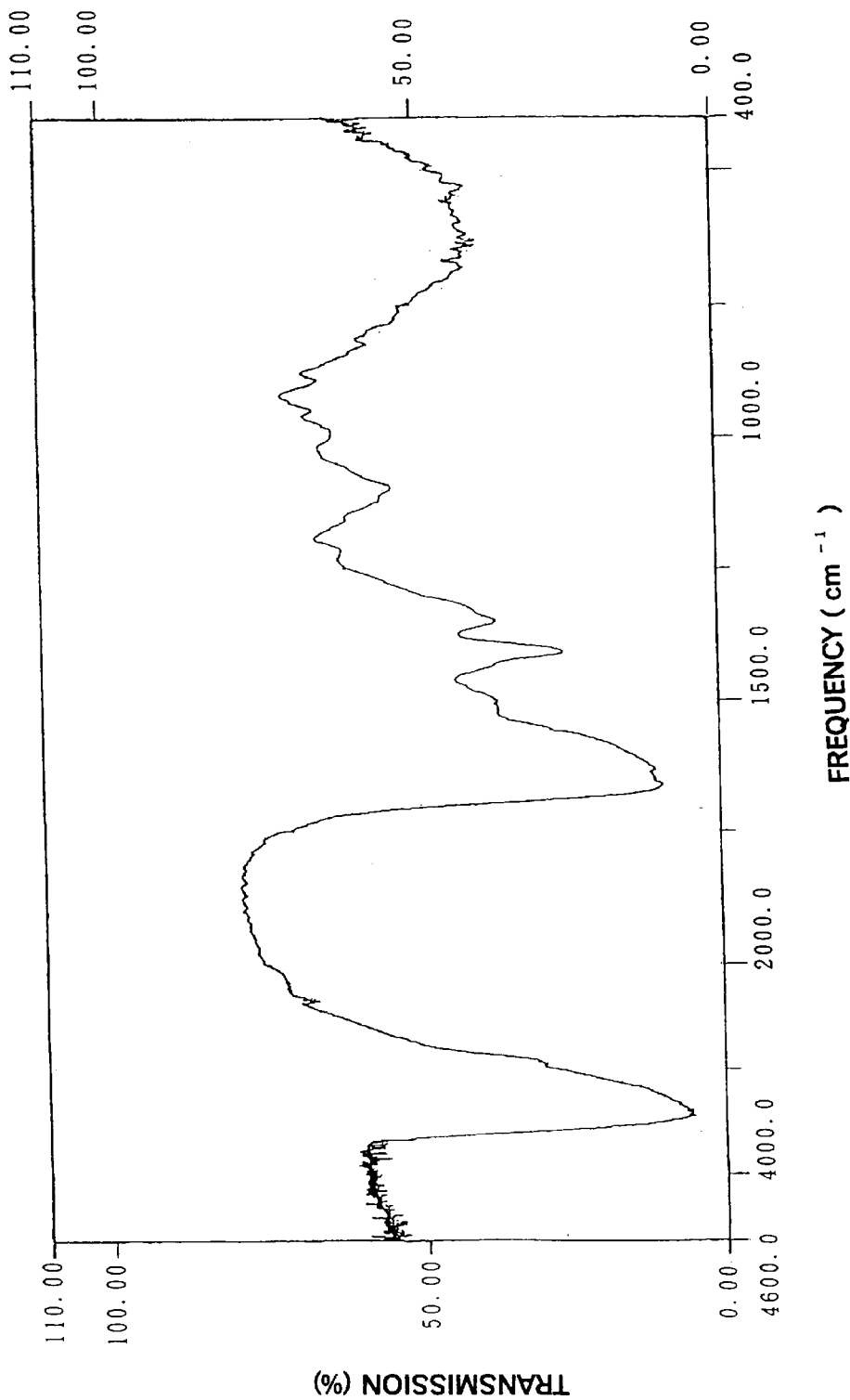
FIG. 2 shows IR spectrum of the MK7634 substance by the KBr method.

The present invention will be explained in detail hereinafter.

The MK7634 substance of the present invention can be obtained by, for example, culturing a microorganism belonging to imperfect fungi and capable of producing the MK7634 substance and collecting the MK7634 substance from its culture. As such a microorganism, though it is not limited to specific ones so long as it has the property mentioned above, a fungus producing the substance and belonging to the genus Curvularia is preferably mentioned. More specifically, Curvularla pallescens D2479 (sometimes referred to simply "the strain" or abbreviated as "D2479" hereinafter), which has been isolated by the present inventors from dead plant bodies, can be mentioned as a preferred fungus producing the substance.

Mycological characteristics of the strain are as follows. This strain was deposited at the Agency of Industrial Science and Technology, the National Institute of Bioscience and Human-technology (NIBH, Postal code: 305, 1-1-3 Higashi, Tsukuba-shi, Ibaraki-ken, Japan) on Nov. 17, 1994 and received an accession number of FERM P-14645, and transferred to international deposition under the Budapest Treaty on Oct. 30, 1995 and received an accession number of FERM BP-5276.

1. Mycological Characteristics of the Strain (D2479)

(1) Morphological Characteristics

As to colony formation, the strain actively forms cotton pile-like colonies in culture at 27° C. for 2 weeks on a potato dextrose agar culture medium [PDA: a culture medium containing 4.0 g of potato extract powder, 20.0 g of glucose and 15.0 g of agar (NISSUI Pharmaceutical) in 1 liter of water (pH 6.0±0.1), NISSUI Pharmaceutical Co., Ltd., Product Summary I, p92], and the colonies present light brown gray color earlier and dark brown later.

Basal hyphae branch, have many partitions and a width of 3.0 to 16 µm and present pale brown to dark brown color.

Chlamydospores are not formed.

Development of aerial hyphae is abundant.

Conidiophores are mononematous, show acrogenesis and pleurogenesis on vegetative hyphae, normally do not branch, but branch sometimes, stand straight or curve, often show zigzag shape at upper portions, present pale brown to dark reddish-brown color, have several partitions, a length of 70 to 450 µm, a width of 3.8 to 5.0 µm, are thin at stems, and swell toward ends.

Poloconidia are formed, and secession marks (scars) are indistinct.

Conidia show fusiform or fusiform rod shape and have 3 partitions, the third cell from the bottom swells, the third cell curves in a comma shape or does not curve, and each cell of conidia presents uniform pale brown, is smooth, and has a size of 17.8 to 31.2×5.3 to 12.0 µm, and conidia have no projecting hilum at their basal parts.

(2) Characteristics in Culture on Various Culture Media

① The strain actively forms colonies in culture at 27° C. for 2 weeks on a malt extract agar culture medium [MA (malt extract agar): a culture medium containing 20.0 g of malt extract, 1.0 g of peptone, 20.0 g of glucose and 20.0 g of agar in 1 liter of water (pH unmodified), Toshikazu Udagawa, Keisuke Tsubaki et al, Illustrated Book of Fungi, Vol. 2, Kodansha, p1281], and colonies present cotton pile-like to velvet-like shape and light brown gray color earlier and grayish black later.

Basal hyphae branch, have many partitions and reach a width of 14.7 μm and present pale brown to reddish brown color.

Chlamydospores are not formed.

Development of aerial hyphae is abundant.

Conidia form abundantly and characteristics of anamorphs of conidiophores and conidia are similar to those observed on PDA culture medium.

② The strain moderately forms colonies in culture at 27° C. for 2 weeks on Miura medium [LCA: a culture medium containing 1.0 g of glucose, 1.0 g of $KH_2PO_4$, 0.2 g of $MgSO_4 \cdot 7H_2O$, 0.2 g of KCl, 2.0 g of $NaNO_3$, 0.2 g of yeast extract and 15.0 g of agar in 1 liter of water (pH 6.5–7.0), the Illustrated Book of Fungus, Vol. 2, supra, p1277], and colonies spread flatly and present cotton pile-like shape and brown gray color earlier and grayish yellow brown color later.

Basal hyphae branch, have many partitions and a width of 2.2 to 10 μm and present pale to pale brown color.

Chlamydospores are not formed.

Development of aerial hyphae is abundant.

Conidia form abundantly particularly in peripheries of colonies and characteristics of anamorphs of conidiophores and conidia are similar to those observed on PDA culture medium.

(3) Physiological Characteristics

Growth temperature (on PDA, 5-day culture): 15 to 35° C.

Optimal temperature: 25 to 30° C.

Growth pH (Miura medium, 7-day culture): 3 to 9

Optimal pH: 5 to 7

(4) Taxonomical Consideration

This strain (D2479) belongs to the genus Curvularia, a group forming poloconidia of the class imperfect filamnetous fungus of the subdivision imperfect fungus, because it is characterized in that 1) it shows poloconidia formation, 2) conidiophores are straight or curved, or often zigzag and conidia form acropetally and 3) conidia have 3 partitions, swelled intermediate cells are always present and some conidia curve in a comma shape. This genus is distinguished from an analogous genus Drechslera because of the characteristics of conidia, i.e., they have true partitions, have 3 to 4 partitions and have swelled intermediate cells.

In the genus Curvularia, 40 or more species have been known. According to Dematiaceous Hyphomycetes, M. B. Ellis (1971), these 40 species are distinguished by difference of host plant and configuration of conidia (presence of hilum of conidium base parts, number of partitions and size, form, presence of inflection of conidia etc.). According to a search list of the species mentioned in Dematiaceous Hyphomycetes, M. B. Ellis, p.452–459 (1971), search of this strain (D2479) at species level was conducted. As a result, the characteristics of the strain well conformed to those of *Curvularia pallescens* and therefore the strain (D2479) was identified as *Curvularia pallescens*. *Curvularia lunata* and *Curvularia leonensis* are mentioned as analogous species, but *Curvularia pallescens* is distinguished from these species by the characteristics shown in Table 1.

TABLE 1

| Characteristics of conidia | D2479 | C. pallescens | C. leonensis | C. lunata |
|---|---|---|---|---|
| Number of Partition | 3 Partitions | 3 | 3 | 3 |
| Swelled cells | The third cell | 3 | 3 | 3 |
| Curved/straight | Curved or straight | Curved or straight | Curved (knee or hook like shape) | Curved |
| Color | All cells are uniformly pale brown | All cells are uniformly pale brown | All cells are uniformly pale brown | Intermediate cells are dark brown; both polar cells are colorless to pale brown |
| Size | 17.8–31.2 × 5.3–12.0 μm | 17–32 × 7–12 μm | 20–32 × 9–13 μm | 20–32 × 9–15 μm |

Characteristics of this strain are likely to change like other fungi. For example, any mutants (naturally occurred or induced), phenotypic zygotes and genetic recombinants of this strain or derived from this strain can be used for the present invention so long as they produce the MK7634 substance.

2. Culturina Method of MK7634 Substance Producing Fungi

A fungus producing the MK7634 substance and belonging to imperfect filamentous fungi is cultured in a culture medium containing nutrients which can be utilized by usual microorganisms. As nutrients, those known for use in conventional culture of fungi can be used. For example, as a carbon source, rice, glucose, starch syrup, dextrin, starch, molasses, animal and vegetable oils and the like can be used. As a nitrogen source, soybean meal, wheat germ, corn steep liquor, cotton seed meal, meat extract, peptone, yeast extract, ammonium sulfate, sodium nitrate, urea and the like can be used. It is also effective to add an inorganic salt capable of producing ions such as sodium, potassium, calcium, magnesium, cobalt, chlorine, phosphate and sulfate ions as required. It is also possible to add any organic or inorganic substance enhancing growth of the fungi and production of the MK7634 substance.

As culturing method, aerobic cultivation, in particular, solid culture methods and submerged culture methods are preferred. A preferred temperature for the cultivation is within 15 to 35° C., but more preferably it is cultured at a temperature around 20 to 30° C. Though the production of the MK7634 substanceldifferently proceeds depending on the culture medium and culture conditions, accumulation of the substance usually reaches maximum within 2–14 days in any of solid culture, shaking culture and tank culture. When the quantity of accumulated MK7634 substance in culture becomes maximum, the cultivation is stopped and the target substance is isolated and purified from the culture medium.

3. Purification Method of MK7634 Substance

The MK7634 substance obtained by the present invention can be collected and purified from a culture of MK7634 substance producing fungi by a separation means utilizing the properties of the substance, for example, solvent extraction, ion exchange resin technique, adsorption or distribution column chromatography, gel filtration, dialysis, precipitation and any combination thereof. For example, the MK7634 substance is extracted from cultured fungi with acetone/water, methanol/water or the like. After evaporating acetone or methanol contained in the extract, the aqueous layer is washed successively with ethyl acetate, n-butanol or the like. By adjusting pH of the aqueous layer around neutral and adsorbing the substance with an ion exchange resin (for example, Diaion PK-208 (H+), Mitsubishi Chemical Corporation, Diaion is a registered trademark), the active ingredient can be eluted with aqueous ammonia or the like. The MK7634 substance can be purified by subjecting a sample obtained by neutralization and lyophilization to gel filtration chromatography utilizing a molecular sieve resin (trade name; Sephadex G-10, Pharmacia) and then gel filtration chromatography utilizing another molecular sieve resin (Toyopearl HW-40S, Tosoh, or the like).

The MK7634 substance can be utilized as an active ingredient of pharmaceutical drugs, in particular, anthelmintics. Examples of creatures that can be administered with the MK7634 substance as an anthelmintic include human and domestic animals, domestic fowls, experimental animals and pet animals such as pig, cow, horse, rabbit, sheep, goat, chicken, duck, turkey, house mouse, albino rat, guinea pig, monkey, dog, cat and birdie. Examples of parasites of these animals include Haemonchus worm, Ostertagia parasitem, hairworm, Cooper nematode, oesophagostomum, strongyloides, aphistome, Benedeen cestode, lungworm, liver hirudinea and the like of cow and sheep, roundworm, whipworm, oesophagostomum of pig, roundworm, hookworm, whipworm, Filarioidea and the like of dog, roundworm, Diphyllobothrium erinacei and the like of cat, roundworm, hairworm, caecum nematode and the like of chicken. Human roundworm, Enterobius, hookworms (Ancylostoma duodenale, Ancylostoma ceylanicum, American hookworm), oriental trichostrongylus, strongyloides, whipworm and the like are also included.

The MK7634 substance can be used for treatment and prevention of various diseases, in particular, treatment and prevention of parasitic infections. Administration for treatment can be done orally or parenterally. When it is orally administered, for example, the substance can be obligatorily administered through a gastric catheter or the like as a liquid drug, or administered by mixing it in usual feed or drinking water, or administered in a usual form suitable for oral administration, for example, tablets, capsules, pellets, boluses, powders and soft capsules. When it is administered parenterally, it can be administered percutaneously, subcutaneously, intramuscularly, intravenously, intraperitoneally or the like as a water-insoluble formulation containing peanut oil, soybean oil or the like or a water-soluble formulation containing glycerol, polyethylene glycol by injection or the like. For the prevention of parasitic infections, the substance is normally administered orally by mixing it in usual feed and the like, or administered by injection. For the prevention of parasitic infections, administration period is not particularly limited and, for example, about 2 months for meat chickens and 5 months for pigs are often sufficient.

Administration dose of the MK7634 substance varies depending on kinds of objective animals and parasites or administration method. For example, 3 mg/kg or more, preferably 6 mg/kg or more is administered when the substance is orally administered as a liquid drug through a gastric catheter in order to get rid of roundworms of chickens. For the prevention, the substance is continuously administered at a concentration of 1 ppm or more, preferably 5 to 10 ppm in feed.

By dissolving or suspending the MK7634 substance in a liquid carrier, it can be administered parenterally by subcutaneous or intramuscular injection or the like to animals. For the parenteral administration, a water-insoluble formulation containing peanut oil, soy bean oil or the like as well as a water-soluble formulation containing glycerol, polyethylene glycol or the like can be used. These formulations generally contains the MK7634 substance at a concentration of 0.1 to 10% by weight. Daily administration dose for parenteral administration is 0.5 mg/kg or more, preferably 1 to 20 mg/kg.

Chickens orally administered with the MK7634 substance show normal weight gain and other anomalies are not recognized. This indicates extremely low toxicity of the substance.

Working examples of the present invention will be described hereinafter. Because the characteristics of the MK7634 substance are clarified by the present invention, various methods for producing MK7634 substance can be established based on the characteristics. Therefore, the present invention is not limited to the following examples and not only any modifications of the examples but also any methods for production, concentration, extraction and purification of MK7634 substance elaborated based on the characteristics of the MK7634 substance revealed by the present invention and utilizing conventional means will fall within the scope of the present invention.

EXAMPLE 1

40 ml each of a culture medium containing 2.0% of starch syrup, 1.0% of soybean meal, 0.15% of soybean oil, 0.25% of Sungrain (Suntory), 0.5% of cotton seed meal, 0.0005% of $FeSO_4 \cdot 7H_2O$, 0.00005% of $NiCl_2 \cdot 6H_2O$, 0.00005% of $CoCl_2 \cdot 6H_2O$ and 0.1% of $CaCO_3$ (pH6.0) was charged in 120 of 200-ml Erlenmeyer flasks and sterilized by autoclaving at 121° C. for 20 minutes. The strain was inoculated to each of these flasks in an amount of one platinum loop and cultured by shaking at 27° C. for 2 days at 210 revolutions per minute.

Separately, 60 g each of rice and 20 ml each of tap water were introduced into 60 of 500-ml Erlenmeyer flasks and sterilized by autoclaving at 121° C. for 20 minutes. To these main culture media, 4 ml each of the above seed culture medium was inoculated and cultured by leaving them stand at 27° C. for 14 days.

90 liters of 50% aqueous acetone was added to the obtained solid culture containing fungi, stirred for 1 hour and isolated the fungi by filtration to afford an extract. The fungi taken by filtration was stirred with the same amount of water for 1 hour and the fungi were separated by filtration to afford an aqueous extract. The above aqueous acetone and the aqueous extract were combined and concentrated under reduced pressure and then the acetone was evaporated to obtain 50.1 liters of an extract. Subsequently, this extract was added with 50 liters of ethyl acetate and washed for one hour by stirring. 50 liters of the aqueous layer was concentrated to 18 liters under reduced pressure, added with the same amount of n-butanol and washed for one hour by stirring. 18 liters of this aqueous layer was concentrated to 13.8 liters under reduced pressure and pH was adjusted to 7.0. This concentrate was adsorbed on a column charged with 2 liters of an ion exchange resin (Diaion PK-208(H+), Mitsubishi Chemical Corporation). The active ingredient was afforded from fractions eluted with 0.5N aqueous ammonia. After adjusting pH to 7.0, 450 ml of this eluate was again adsorbed on a column charged with 1 liter of an ion exchange resin (Diaion PK-208(H+), Mitsubishi Chemical Corporation) and chromatographed with a concentration gradient formed by 1 liter of purified water and 1 liter of 0.5N aqueous ammonia, and 15 ml fractions were collected. 8.5 g of active fraction was obtained from fractions No. 46 to No. 129. This was dissolved in 250 ml of purified water, adjusted to pH 7.0 and adsorbed on a column charged with 330 ml of an ion exchange resin (Diaion PK-208(H+), Mitsubishi Chemical Corporation). Chromatography was performed using a concentration gradient formed with 700 ml of purified water and 700 ml of 0.5 N aqueous ammonia to collect 5 ml fractions. Fractions No.169 to No.240 were collected to afford 5.5 g of active fraction.

Then, 2 g of the above active fraction was dissolved in 50 ml of purified water, subjected to column chromatography using a column charged with 830 ml of a molecular sieving resin (Sephadex G-10, Pharmacia) and purified water at pH 7.9 and fractionated into 3 ml fractions. Fractions No. 49 to No. 53 were collected to afford 124 mg of an active fraction. Similarly, 1.0 g out of 5.5 g of the above active fraction was dissolved in 20 ml of purified water, subjected to column chromatography using a column charged with 470 ml of a molecular sieving resin (Sephadex G-10, Pharmacia) and purified water at pH 7.9 and fractionated into 2 ml fractions. Fractions No. 19 to No. 30 were collected to afford 145 mg of an active fraction. This 145 mg of active fraction was combined with the previously obtained 124 mg of active fraction, dissolved in 10 ml of purified water, adjusted to pH 7.3, subjected to column chromatography using a column charged with 480 ml of a molecular sieving resin (Sephadex G-10, Pharmacia) and purified water and fractionated into 2 ml fractions. Fractions No. 49 to No. 55 were collected to afford 84 mg of an active fraction.

This 84 mg of active fraction was dissolved in 5 ml of purified water, adjusted to pH 7.25, subjected to column chromatography using a column charged with 340 ml of a molecular sieving resin (TOYOPEARL HW-40S, Tosoh) and purified water and fractionated into 2 ml fractions. Fractions No. 38 to No. 52 were collected and lyophilized to afford 7.2 mg of the MK7634 substance as colorless powder.

Similarly, 2.5 g out of the above 5.5 g of the active fraction afforded by the chromatography utilizing the above ion exchange resin (Diaion PK-208(H+), Mitsubishi Chemical Corporation) was dissolved in 60 ml of purified water, subjected to column chromatography using a column charged with 830 ml of a molecular sieving resin (Sephadex G-10, Pharmacia) and purified water at pH 7.4 and fractionated into 3 ml fractions. Fractions No. 24 to No. 36 were collected to afford 203 mg of an active fraction. This 203 mg of active fraction was dissolved in 10 ml of purified water, adjusted to pH 7.3, subjected to column chromatography using a column charged with 600 ml of a molecular sieving resin (Sephadex G-10, Pharmacia) and purified water and fractionated into 2 ml fractions. Fractions No. 37 to No. 47 were collected to afford 74.7 mg of an active fraction. This 74.7 mg of active fraction was dissolved in 6 ml of purified water, adjusted to pH 7.3, subjected to column chromatography using a column charged with 340 ml of a molecular sieving resin (TOYOPEARL HW-40S, Tosoh) and purified water and fractionated into 2 ml fractions. Fractions No. 56 to No. 67 were collected and lyophilized to afford 4.0 mg of the MK7634 substance as colorless powder.

Figure 3:
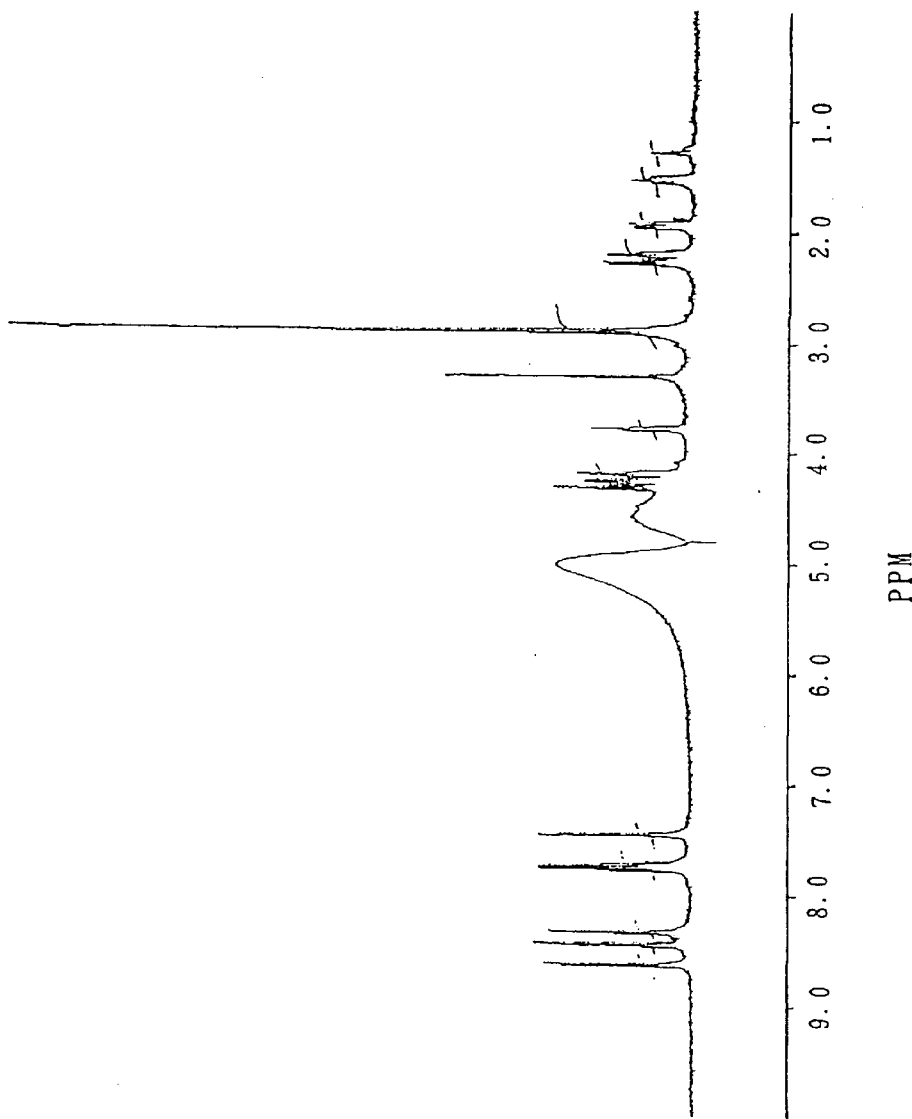
FIG. 3 shows $^1$H-NMR spectrum (400 MHz) of monodansylated MK7634 substance in a mixed solution of deuterium oxide and deuterated methanol (mixing weight ratio=4:1).
Figure 4:
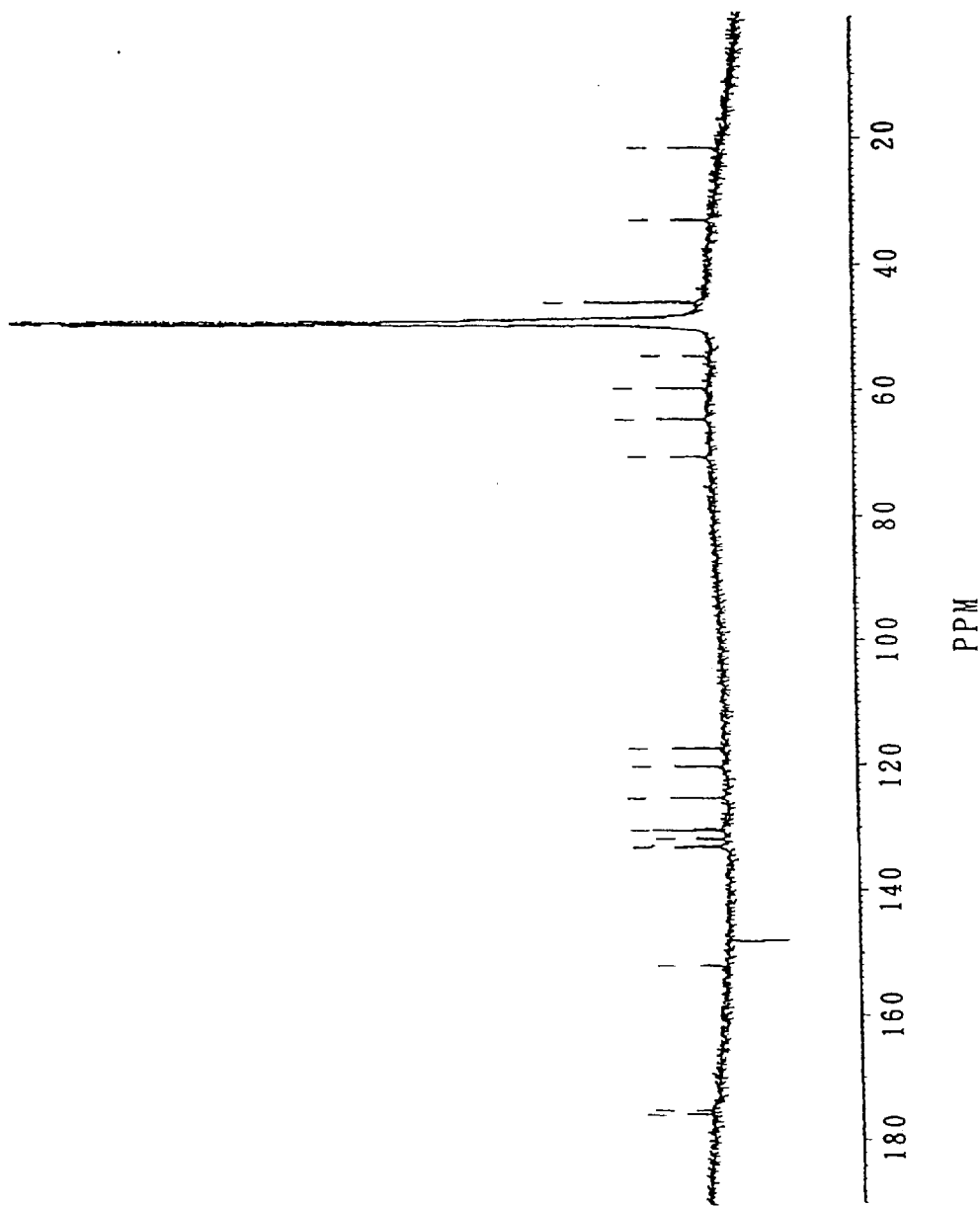
FIG. 4 shows $^{13}$C-NMR spectrum (100 MHz) of monodansylated MK7634 substance in a mixed solution of deuterium oxide and deuterated methanol (mixing weight ratio=4:1).

Physicochemical characteristics of the MK7634 substance corresponded to those described above. The molecular weight and the molecular formula were obtained by determining high resolution mass spectrum of a monodansylated compound of the substance, which was obtained by dansylating the substance. Values of chemical sift and association constant according to $^1$H-NMR (FIG. 3) and values of chemical sift according to $^{13}$C-NMR (FIG. 4) of the MK7634 substance in a mixed solvent of deuterium oxide and deuterated methanol (weight mixing ratio=4:1) are shown below.

$^1$H-NMR δ(ppm); 8.63 d(1H, J=8 Hz), 8.45 d(1H, J=8 Hz), 8.33 d(1H, J=8 Hz), 7.75 m(2H); 7.46 d(1H, J=8 Hz), 4.26 m(3H); 3.80 t(1H, J=3 Hz), 2.90 s(6H), 2.28 m(2H), 1.97 m(1H), 1.56 m(1H); $^{13}$C-NMR δ(ppm); 175.7, 175.1, 151.7, 133.0, 132.7, 131.6, 130.3, 130.2, 129.9, 125.1, 120.1, 117.3, 70.5, 64.5, 59.6, 54.5, 45.9, 33.0, 21.5

EXAMPLE 2

A chicken artificially infected with chicken roundworms, whose chicken roundworm infection had been confirmed by fecal smear examination, was used as one group for each of four density grades. Five chickens in total including one no medication group were examined. The MK7634 substance was orally administered at one time by a feeding tube as a gelatin capsule containing a dose accurately calculated based on body weight of each chicken. After administration, number of discharged roundworms was counted for each chicken every day and, 7 days later, each chicken was dissected to count the residual number of the worm in the bowel and calculate the worm discharging ratio.

Worm discharging ratio=[Number of discharged worms in 7 days/ (Number of discharged worms in 7 days+Number of residual worms in bowel)]×100

Body weight of each chicken was measured immediately before the administration and 7 days after the administration and body weight increasing ratio was calculated.

Body weight increasing ratio=[(Body weight 7 days after administration−Body weight upon administration)/Body weight upon administration]×100

The results of the above examination are shown in Table 2. The MK7634 substance showed a worm discharging ratio of 97.4% at 6.06 mg/kg. The body weight increasing ratio was almost equal to that of no medication control even when this substance was administered at 31.9 mg/kg and hence it was confirmed that the MK7634 substance was a relatively safe drug.

TABLE 2

Chicken roundworm discharging test by MK7634 substance administration

| Chicken No. | Administration dose (mg/kg) | Worm discharging ratio (%) | Body weigh increasing ratio (%) |
|---|---|---|---|
| 1 | No medication | 0 | 18.0 |
| 2 | 2.89 | 61.3 | 49.3 |
| 3 | 6.06 | 97.4 | 16.4 |
| 4 | 15.3 | 100 | 23.4 |
| 5 | 31.9 | 100 | 25.0 |

Industrial applicability

The MK7634 substance of the present invention is expected to be used as an anthelmintic against parasites in humans and/or domestic animals and fowls and the like.

What we claimed is:

1. Isolated MK7634 compound which is basic and water-soluble and has the following physicochemical properties:

(1) Color and form: Colorless powder (2) Molecular formula: $C_8H_{15}N_3O_4$ (3) Specific rotation: $[\alpha]D^{25}=+32.8°$ (c=0.5, $H_2O$)

(4) Mass spectrum (secondary ion): m/z 240 (MNa)+, 218 (MH)+

(5) Ultra-violet absorption spectrum: λmax ($H_2O$) nm=193 (end absorption)

(6) Infra-red absorption spectrum: νmax (KBr) $cm^{-1}$= 3400, 1670, 1630, 1405, 1350, 1090, 970

(7) Melting point: gradually colored and decomposed from 175° C.

(8) Solubility: soluble in water and insoluble in ether, chloroform and ethyl acetate (9) basicity, acidity and neutrality: basic

(10) Color reaction: positive in ninhydrin, GL and molybdic acid reactions

(11) Thin layer chromatography: Rf value is 0.3 when the developing solvent is a mixed solvent of n-butanol, ethanol, chloroform and 17% ammonia, wherein the weight mixing ratio is 4:5:2:5.

2. The MK7634 compound of claim 1, wherein the compound is isolated from the deposited cell line of *Curvularia pallescens* available under accession number FERM BP-5276.

3. A pharmaceutical composition comprising compound MK7634 of claim 1 and a pharmaceutically acceptable carrier.

4. The pharmaceutical composition of claim 3, wherein the compound MK7634 is isolated from the deposited cell line of *Curvularia pallescens* available under accession number FERM BP-5276.

5. The pharmaceutical composition of claim 3, wherein the compound is anthelmintic.

6. A process for producing MK7634 compound, which comprises culturing a *Curvularia pallescens* that produces the MK7634 compound of claim 1 in an aqueous nutrient medium containing assimilable sources of carbon, nitrogen and inorganic substances, and collecting the MK7634 compound from its culture.

7. The process of claim 6, wherein the *Curvularia pallescens* is the deposited cell line available under accession number FERM BP-5276.

* * * * *